(12) United States Patent
Nguyen et al.

(10) Patent No.: US 6,984,524 B2
(45) Date of Patent: Jan. 10, 2006

(54) CHEMILUMINESCENT DETECTION OF EXPLOSIVES, NARCOTICS, AND OTHER CHEMICAL SUBSTANCES

(75) Inventors: Dao Hinh Nguyen, Ottawa (CA); Stewart Berry, Ottawa (CA); Jan Prot Geblewicz, Toronto (CA); Guy Couture, Ottawa (CA); Phuong Huynh, Ottawa (CA)

(73) Assignee: Control Screening, LLC, Fairfield, NJ (US)

( * ) Notice: Subject to any disclaimer, the term of this patent is extended or adjusted under 35 U.S.C. 154(b) by 621 days.

(21) Appl. No.: 10/241,407

(22) Filed: Sep. 12, 2002

(65) Prior Publication Data

US 2004/0053421 A1 Mar. 18, 2004

(51) Int. Cl.
*G01N 21/76* (2006.01)
(52) U.S. Cl. .................. 436/107; 436/110; 436/172; 422/52; 422/80; 422/82.05; 250/361 C
(58) Field of Classification Search ............ 422/52, 422/82.05, 82.08, 78, 80; 436/106, 107, 436/110, 155, 156, 166, 172, 174, 177; 250/458.1, 250/459.1, 361 C
See application file for complete search history.

(56) References Cited

U.S. PATENT DOCUMENTS

| | | | | |
|---|---|---|---|---|
| 4,765,961 A | | 8/1988 | Schiff et al. ................... 422/52 |
| 5,015,590 A | | 5/1991 | Kinrade ....................... 436/117 |
| 5,092,220 A | * | 3/1992 | Rounbehler ................... 89/1.1 |
| 5,364,795 A | * | 11/1994 | Sausa et al. ................. 436/106 |
| 5,395,589 A | | 3/1995 | Nacson ........................ 422/88 |
| 5,424,216 A | | 6/1995 | Nagano et al. ............. 436/116 |
| 5,476,794 A | * | 12/1995 | O'Brien et al. ............... 436/92 |
| 5,638,166 A | * | 6/1997 | Funsten et al. ............... 356/36 |
| 5,760,898 A | * | 6/1998 | Haley et al. ................. 356/318 |
| 6,100,096 A | * | 8/2000 | Bollinger et al. ........... 436/116 |
| 6,245,576 B1 | * | 6/2001 | Hiley ......................... 436/110 |
| 6,797,944 B2 | * | 9/2004 | Nguyen et al. ............. 250/286 |
| 2003/0100123 A1 | * | 5/2003 | Schanze et al. ............. 436/106 |

(Continued)

OTHER PUBLICATIONS

Haley, L.V. et al. "Laser Based Explosives Detection" IEEE (2000), pp. 207-217.*

(Continued)

*Primary Examiner*—Jeffrey R. Snay
(74) *Attorney, Agent, or Firm*—Ernest D. Buff & Associates,LLC; Ernest D. Buff; Gordon E. Fish

(57) ABSTRACT

A compact scanning apparatus has an infrared laser adapted to emit light. The light is delivered as a beam by an optical system to illuminate an interrogation area on the surface of an object being scanned. Such illumination has sufficient intensity and duration to cause selective desorption of molecules of the contraband substance, which are present on the surface, without substantially damaging the surface. A collection system collects at least a portion of the desorbed molecules. At least a portion of the collected molecules is thermally decomposed to form $NO_2$ and transferred to a reaction cell containing an aqueous, alkaline, luminol-containing solution. The $NO_2$ reacts with the luminol to produce light by chemiluminescence. A light detector registers the presence of this light as indicative of the detection of the contraband substance, and activates a signaling device to provide an audible or visible alarm. The apparatus rapidly detects the presence of a wide variety of contraband substances in an accurate, reliable manner. It provides for automated screening, with the result that vagaries of human performance are virtually eliminated. False alarms are reduced and detection efficacy is increased. A traceable residue of the detected contraband is left on the article for use in forensic analysis.

40 Claims, 7 Drawing Sheets

U.S. PATENT DOCUMENTS

2003/0143119 A1 * 7/2003 Schwartz et al. ......... 422/82.08
2004/0051867 A1 * 3/2004 Brestel et al. .............. 356/318

OTHER PUBLICATIONS

Arusi-Parpar, T. et al. "Photodissociation followed by laser induced fluorescence at atmospheric pressure and 24 oC: a unique scheme for remote detection of explosives" Applied Optics, vol. 40 (Dec. 12, 2001), pp. 6677-6681.*

Maeda et al. "Chemiluminescence Method for the Determination of Nitrogen Dioxide," Anal. Chem. vol. 52, p.p.307-311.

Capellos et al., "Infrared Multiphoton Decomposition of 1,3,5-Trinitrohexahyo-S-Triazine," Advances in Chemical Reaction Dynamics, ed. Rentzepis et al., 1986, p.p. 395-404.

Winberry, Jr. et al. *Compendium of Methods for the Determination of air Pollution in Indoor Air*, EPA Report EPA/600/4-90/010, 1990, Chapter IP-5.

Rounbehler et al., "Analysis of Explosives Using High Speed Gas Chromatography With Chemiluminescent Detection," Proceedings of the First International Symposium on Explosive Detection Technology, Feb. 1992, p.p.703-707.

Hao et al. "Gas Chromatographic Detector for Selective and Sensitive Detection of Atmospheric Organic Nitrates," Analytical Chemistry, vol. 66, No. 21, Nov. 1, 1994, p.p. 3737-3743.

Easton et al., "Quantitative Model of the Enhancement of Peroxidase-Induced Luminal Luminescence," journal of the American Chemical Society, 1996, vol. 18, p.p. 6619-6624.

Thermo Detection: http://www.thermo.com/eThermo/CDA/Products/Product_Detail/1/1075.14817.00.html.

Unisearch Associates, Inc: http://www.unisearch-associates.com/luminox.htm.

* cited by examiner

CHEMILUMINESCENT DETECTION OF EXPLOSIVES, NARCOTICS, AND OTHER CHEMICAL SUBSTANCES

BACKGROUND OF THE INVENTION

1. Field of the Invention

This invention relates to the field of scanner apparatus and methods; and more particularly to inspection systems that scan luggage and cargo to detect residues of explosives or other contraband materials.

2. Description of the Prior Art

In recent years, the prevalence of criminal activity that entails transportation of weapons and contraband materials has been a significant public concern. It has thus become vital to develop systems for detecting the presence of these materials, both when shipped as luggage or cargo and when carried by an individual. Of particular concern is the need to detect items used as weapons by terrorists, including ordinary firearms and knives, items such as explosive or incendiary substances, and materials which present biological, chemical or radiological hazards to people and property. The detection of illicit drugs and narcotics being transported is also of concern.

The detection of contraband in the context of air and rail transportation is especially challenging, given the need to examine large numbers of people and articles of luggage and cargo within acceptable limits on throughput and intrusiveness. Although physical inspection is a widely practiced and important technique, it is slow, cumbersome, labor intensive, and dependent on the alertness and vigilance of the inspector.

Automated systems that screen for contraband have been sought for many years. Various techniques have been proposed to detect contraband objects and materials either directly or indirectly. Magnetometry is widely used, and is sometimes effective in detecting metallic objects carried by persons, but is not suited for screening cargo, which legitimately may contain large amounts of metal. Nuclear techniques, including x-ray, gamma-ray, neutron activation, and nuclear magnetic resonance methods, are applicable for screening inanimate objects, but pose risks that generally preclude their use for screening humans. In some cases, they are able to detect metallic objects, including weapons and ancillary devices such as wires, power supplies, batteries, and triggering mechanisms for explosive devices. However, there increasingly exist threats posed by explosives associated with largely non-metallic objects, which the aforementioned methods are less able to detect. The advent of modern plastic explosives presents an especially significant threat. Even a modest, readily concealable amount of these substances can cause a substantial explosion. Moreover, miscreants have become increasingly adept at disguising weapons and explosive devices as ordinary, innocuous objects. As a result, more refined indirect methods for detection of explosives are urgently sought.

Many of the indirect methods rely on the presence of vapor emanating from suspect material. One such indirect method, widely used in law enforcement, employs dogs trained to sniff preferentially for explosives, drugs, and the like. The remarkable olfactory sensitivity of dogs has been known and exploited for centuries. However, they are subject to fatigue, behavior variations, and the need for careful handling, training, and reinforcement from their masters. It therefore remains highly desirable to have luggage scanning systems that are not subject to these limitations. Also needed are luggage and cargo scanning systems that rapidly and accurately discriminate among different substances and indicate the quantity and location of a critical substance.

The task of indirectly detecting the presence of suspect materials is further complicated by their wide variability in vapor pressure. Some explosives, including nitroglycerin (NG), dynamite, EGDN, and EGTN, are comparatively volatile, exhibiting significant vapor pressure at room temperature. DNT and TNT have lower, but still appreciable room-temperature vapor pressure. However, some of the most critical materials for which detection is sought, e.g. drugs, such as cocaine and heroin, and plastic explosives, such as SEMTEX and C-4, are far less volatile, having room temperature vapor pressures as much as ten million times lower. It is virtually impossible to detect vapor naturally emanating from these low volatility materials. They are even more difficult to detect if sealed inside luggage or packaging.

It is known that certain contraband materials for which detection is sought are inherently sticky. This characteristic is a notable property of many plastic explosives. As a result, particulate residues are likely to be present (i) on the hands of a person who has even casually handled the contraband, even after repeated hand washing, (ii) in fingerprints on surfaces such a person has subsequently touched, and (iii) as cross-contamination on the surface of a vehicle, shipping container, or luggage in which the material has been placed. For example, a measurable amount of ammonium nitrate (AN) residue has been found on the lease documents for rental trucks; and significant amounts of the explosives PETN (pentaerythritol tetranitrate) and/or AN have also been found on clothing and inside vehicles of suspects in two well-publicized bombings. Therefore, explosive residue will likely persist in large amounts on the explosive packaging and its environs, as well as on the individuals involved in building, handling, and transporting the explosive device, thereby providing an avenue for detection of the presence of explosives. The detection of even trace residues of critical substances on a person, article, or vehicle suggests a strong likelihood of association with illicit activity warranting further investigation.

The dual challenges of sample collection and analysis continue to impede development of satisfactory screening systems for the aforesaid contraband materials. As previously described, many of the materials whose detection is most critical have extremely low vapor pressure. The equilibrium concentration in the atmosphere near a contaminated fingerprint may be only parts per billion or trillion, a value too low for known detection schemes. Hence, previous detection methods have frequently employed mechanical means for collecting and/or concentrating a sample to achieve detectability. In some cases, disposable swabs or wipes of dry paper or cloth are rubbed by an operator against luggage or shipping containers to pick up detectable amounts, if any, of particulate residue. Such wipes may also be wetted with a solvent to facilitate residue pickup. In either case, the wipe is subsequently transferred to a suitable detection system for chemical analysis.

If carried out with rigorous attention to collection protocols, wipe techniques provide an effective method of manually collecting samples from the surface of objects. However, known wipe systems have a number of significant limitations. They generally require an operator and are not conveniently adapted to automation. Their throughput is limited by the cumulative time needed for the essential multiple operations—in addition to the actual analytical time, the process requires the prior intermediate steps of wiping the article under test and transferring the wipe to the detection system. The detection efficacy and success of wipe systems is generally dependent on human factors. Stress and the frequent confusion extant in a busy public facility may cause an operator to fail to carry out an adequate sampling. The wiping operation frequently fails to cover a sufficiently representative portion of an article to insure that whatever residues are present are actually captured. Lint, dirt, solvent, and other extraneous material of no interest are inevitably introduced into the detection system. In some cases these contaminants reduce the system's sensitivity by diluting the concentration of the analyte and necessitating frequent, non-productive cleaning operations.

Other known systems have employed mechanical brushing or shaking of articles or impingement of a compressed gas stream to dislodge residue particles. While these methods are more amenable to automation than wiping-based methods, they still are not sufficiently fast and efficacious for the demanding requirements of inspecting items to be carried as cargo or hand luggage on aircraft, for example. Furthermore, regulation of the pressure and volume of the gas stream is a significant challenge, as the flow must be sufficient to dislodge particles but not so high that it is not possible to capture what is removed.

Systems have also been proposed for detecting the presence of residues on a human subject passing through a tunnel-like portal. The portal may include means for flowing gas across the subject to dislodge particulate residues, collecting the gas, filtering or otherwise concentrating the particulates to above a detection limit, and passing the concentrated sample to a suitable detector. However, improvement in these systems is still desired. Flowing gas is at best an inefficient vehicle for collecting adequate sample. Disruptions of the airflow owing to the motion of subjects passing through the portal further compromise sample collection. In addition, the need to pre-concentrate a sample limits the analysis rate, making it difficult to reliably associate detection of contraband substances of interest with a specific person passing through the sampling portal.

Each of the indirect screening systems previously discussed requires means for sample collection and analysis that discriminate suspect substances from components normally present in the atmosphere. To be effective, the sample collection and analysis means must additionally discriminate suspect substances from the myriad of vapors produced by items of ordinary commerce.

A number of vapor detection methods have been proposed. These vapor detection methods have found use in laboratory analysis. Among them are electron capture detection, gas chromatography detection, mass spectrometry detection, plasma chromatography detection, bio-sensor detection and laser photoacoustic detection.

There have also been suggested systems for detecting explosive residues that do not rely on vapor detection. One example is the use of a controlled burst of laser radiation to induce selective deflagration or micro-detonations of explosive residues on the surface of an article. The resulting reaction produces an optical signature characteristic of the explosive residue. The system relies on detection of this optical signature. As used herein, the term "deflagration" means a slow chemical oxidation of the material, with a burn front which propagates at less than the velocity of sound. The term "detonation" as used herein means a reaction similar to deflagration that occurs at a much faster rate. Detonation is characterized by wave propagation at a supersonic rate with respect to the unreacted material.

Notwithstanding the aforementioned schemes both for sample collection and analysis, there remains a need in the art for integrated systems capable of reliably, accurately, and rapidly detecting the presence of contraband substances, especially explosives, accelerants, and illicit drugs. More particularly, there is need for systems that are readily automated for semi-continuous or continuous inspection and detection of the presence of residues of such materials on luggage, cargo, vehicles, freight containers, and related items. Such systems are highly sought, especially in the context of airport screening, but would be equally valuable for courthouses, stadiums, schools, government offices, military installations, correctional institutions, and other public venues that might be targets of terrorist or similar criminal activity.

SUMMARY OF THE INVENTION

The present invention provides a method and system for detecting small quantities of explosives and other contraband substances located on the surfaces of objects. The technique employs a chemical reaction between $NO_2$ gas and luminol in an aqueous, alkaline solution. Under suitable conditions, the vast majority of common explosive types may be decomposed to produce $NO_2$ gas that is detected using the apparatus presented herein. The luminol reaction is known to produce light by a process termed chemiluminescence. This light, in turn, is detected to signal the presence of the contraband substance.

The use of the luminol reaction enables a compact scanning system in accordance with the present invention to detect the presence of a wide variety of contraband substances in an accurate and reliable manner. The system rapidly and accurately discriminates among different substances and provides quantitative indication of the amount and location of a critical substance. It is especially well suited for use in applications which require high throughput and accuracy, such as security screening associated with airline and other forms of public transportation.

Advantageously, the system provides in some aspects for automated screening. It can be configured to automatically scan substantially the entire exterior surface of luggage and other hand-carried personal items, as well as cargo, without the need for hand wiping or sampling by an operator or other physical contact. Vagaries of human performance are virtually eliminated, and detection efficacy is improved. The system's greater speed, accuracy, reliability, and flexibility, as well as its lower cost, and expanded range of detectable substances overcome problems associated with commercial scanning systems. Importantly, the system of this invention markedly reduces or eliminates false alarms while maximizing detection sensitivity for actual contraband. Following detection of contraband, a traceable residue thereof is left on the article for use in subsequent forensic analysis by law enforcement or other agencies.

More specifically, the present invention is directed to a method and system for the detection of contraband substances, including those present on the surface of baggage items. As used herein, the term "baggage item" is intended to include non-exclusively objects such as luggage, suitcases, cargo, freight, boxes, cartons, envelopes, crates, packages, personal articles, and the like, appointed for transport on aircraft, rail, ship, bus or other like public conveyance.

Generally stated, the method comprises the steps of: (i) producing $NO_2$ by decomposition of at least a portion of the contraband substance; (ii) transferring the $NO_2$ to a reaction cell, a portion of which contains an aqueous, alkaline luminol solution; (iii) reacting, within a reaction cell, the $NO_2$ with luminol in the presence of $O_2$ to produce light by chemiluminescence; and (iii) detecting the light with a light detector to indicate the presence of the contraband substance.

The system of the invention can detect the presence of a wide variety of contraband substances. As used herein, the term "contraband" is intended to denote substances or articles whose transportation or possession is forbidden or improper. A wide variety of substances or articles may be considered as contraband, including non-exclusively: firearms and similar weapons; explosives and explosive devices; incendiaries, propellants, and accelerants; drugs such as heroin, cocaine, opium and its derivatives and other narcotics, cannabis (including marijuana and hashish), amphetamines and barbiturates; hallucinogens and psychotropics; and other substances and articles which present biological, chemical or radiological hazards to people and property. In general, any of these materials which may be decomposed to produce $NO_2$ may be detected.

In one aspect of the invention there is provided a system for screening at least a portion of the surface of a baggage item for the presence thereon of a contraband substance. The system comprises: (i) an infrared laser adapted to emit light; (ii) an optical system adapted to deliver a beam of the laser light to illuminate an interrogation area of the surface, the illumination having sufficient intensity and duration to cause selective desorption of molecules of the contraband substance present on the surface without substantially damaging the surface, and at least a portion of the molecules being thermally decomposed to produce $NO_2$ molecules; (iii) a collection system having an aperture and being adapted to collect at least a portion of the desorbed molecules through the aperture; (iv) a reaction cell in communication with the collection system, the reaction cell having a reaction zone, an inlet for receiving in the reaction zone the molecules collected by the collection system, an outlet for release of the air, and the reaction cell containing an alkaline, aqueous luminol-containing solution; (v) a light detector to detect light produced chemiluminescently by a chemical reaction between the luminol and the $NO_2$ within the reaction cell and to output an electrical signal indicative of the detection of the light; and (vi) signal means for indicating the presence of the $NO_2$ produced by the decomposition of the contraband substance, the signal means being operably connected to the light detector and responsive to the receipt of the electrical signal.

In some implementations, the invention further comprises means for relative motion of the baggage item and the laser light beam, thereby permitting an extended interrogation zone to be scanned for explosives. As a result, the system may easily be automated for use in applications that require high throughput and accuracy, such as security screening associated with airline and other forms of public transportation. The system provides for automated screening that can scan substantially the entire exterior surface of luggage and other hand-carried personal items, as well as cargo, without the need for hand wiping or sampling by an operator or other physical contact. Real time automated detection is thereby accomplished in an accurate, reliable manner. As a result, the inevitable vagaries of human performance are virtually eliminated, improving the efficacy of detection. The present system is also useful for screening in other contexts, including courthouses, stadiums, schools, government offices, military installations, correctional institutions, and similar public venues that might be targets of terrorist or similar criminal activity. The combination of speed, accuracy, reliability, flexibility, low cost, and range of critical substances detectable solves problems associated with prior art scanning systems and renders the present invention highly advantageous. Furthermore, the present invention markedly reduces or eliminates false alarms while maximizing the probability of detection of actual contraband.

The present system is also capable of detecting the presence of contraband in a nondestructive manner, such that the surface being studied is left substantially undamaged as a result of being scanned by the present laser desorption system. That is, the appearance and function of the scanned surface is not harmed. Although in some cases, minimal changes may occur that are detectable only by microscopic or other sophisticated analytical means, the overall presentation of the article to the ordinary human senses is unaffected.

The disclosed method further comprises an optional pyrolysis step that produces additional $NO_2$, predominantly by pyrolyzing particles ablated by the impingement of the laser light. Sufficient $NO_2$ is produced to be detectable using the luminol reaction, thereby rendering the presence of the contraband substance detectable, even if the amount thereof is quite limited. The specific minimum amount of explosive or other contraband that is detectable depends on the material, but may be as low as the sub-nanogram level. The interrogation area may be substantially the spot size of the beam. Alternatively the beam may be variably deflected or the object moved to vary the point of impingement, thereby extending the interrogation area generally to a linear region or an extended, two-dimensional area. It is preferred that the interrogation zone comprise at least a substantial portion of the object under scrutiny. The ejected material is collected in a collection system and analyzed by a chemical analysis system adapted to detect the presence of at least one contraband substance. An audible or visual indication is provided upon detection of a contraband substance.

The present system is adapted for the detection of a wide variety of contraband substances for which detection is desired. The chemical analysis systems disclosed herein can be readily be adjusted and suitably calibrated and operated to be sensitive and selective for detection of such materials, notably including modern explosive materials such as C4, SEMTEX, and DM12.

BRIEF DESCRIPTION OF THE DRAWINGS

The invention will be more fully understood and further advantages will become apparent when reference is had to the following detailed description of the preferred embodiments of the invention and the accompanying drawings, wherein like reference numerals denote similar elements throughout the several views, and in which.

DESCRIPTION OF THE PREFERRED EMBODIMENTS

Figure 1:
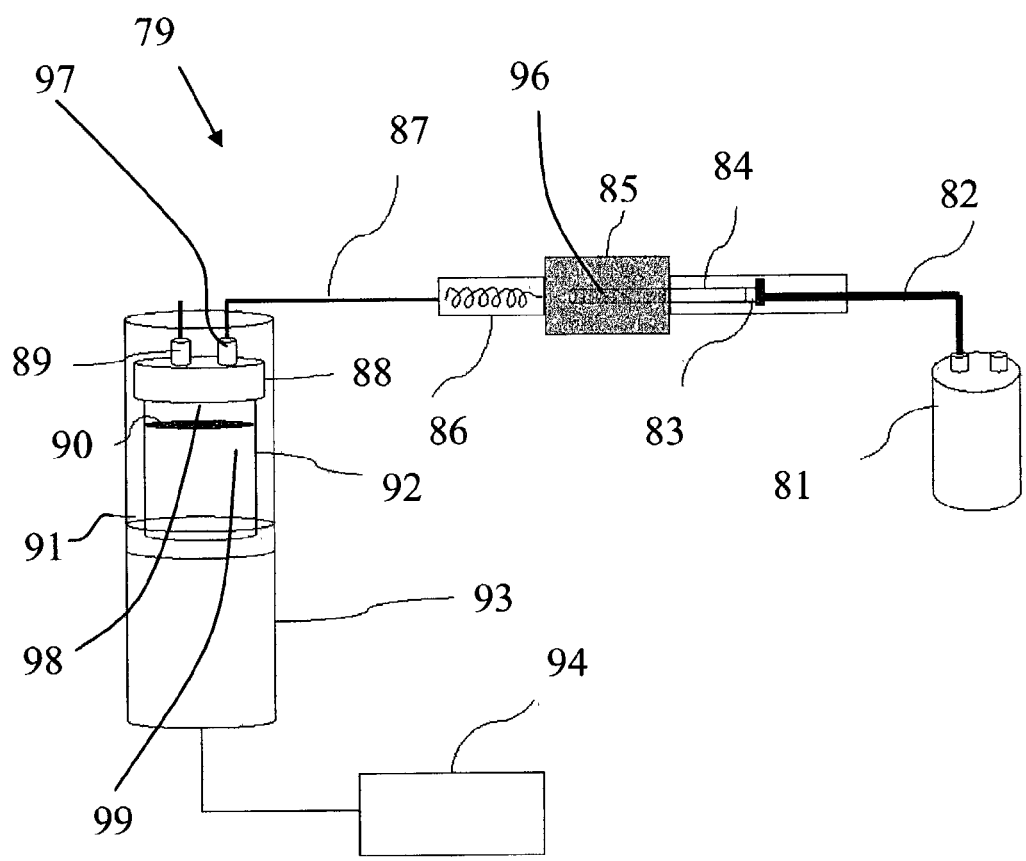
FIG. 1 is a schematic view of an explosive detection system of the invention using a removable collection tube.

The present invention provides an apparatus and method for analyzing surface residue suspected of containing one or more explosive agents or other contraband substances using the chemiluminescent, gas-liquid phase reaction of luminol and $NO_2$.

Virtually all common explosive types, including organo-nitro explosives, as well as many other contraband substances of interest may be decomposed under suitable conditions to produce $NO_2$. In one aspect of the invention, the decomposition comprises pyrolysis according to reactions of the following type:

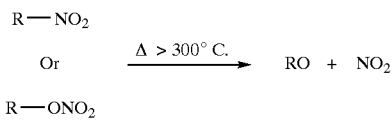

The pyrolysis reaction ordinarily requires a suitable catalyst for efficient production of $NO_2$. It has been found that suitable catalysts include heated Nichrome or Pt, while a heated Pt—Rh alloy is preferred. The catalyst preferably has the form of a wire that is electrically heated to a temperature ranging from about 300 to 800° C., and more preferably, to a temperature ranging from about 500 to 700° C. Pyrolysis does not occur if the temperature is too low, while excessive power is required to raise the temperature too high. Power consumption is also preferably limited by pulse heating the catalyst. Moreover, adjustment of the peak temperature allows selective optimization of the sensitivity of the system to different nitrogen-bearing substances. The optimal catalyst temperature will also vary to some degree depending on pulse duration.

In another aspect described hereinbelow in more detail, $NO_2$ is released from explosive residue on the surface of an object by thermal decomposition resulting from the impingement of laser light thereon. It will be understood that other means may also be used to decompose contraband substances to produce detectable $NO_2$ and are within the scope of the present invention. In addition, the invention provides for the detection of ambient $NO_2$ from other sources.

Luminol (5-amino-2,3-dihydro-1,4-pthalazine dione) is known to react with $NO_2$ in the presence of oxygen to produce light at a wavelength centered at about 425 nm according to the following reaction:

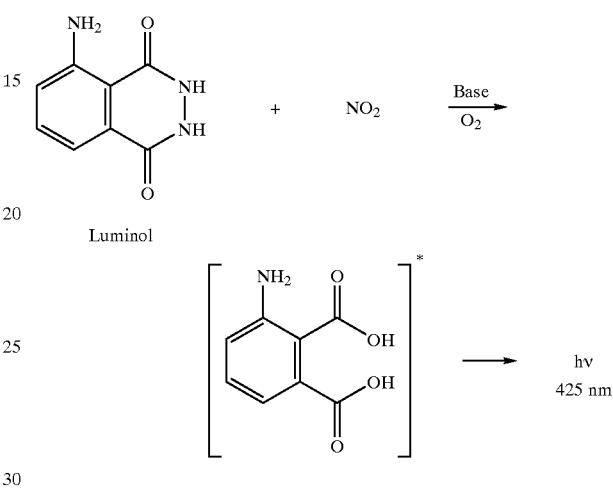

The light thereby produced can readily be detected by a light detector, such as a photomultiplier tube (PMT). Advantageously, conventional PMT's are quite sensitive to light of this wavelength.

Moreover, this chemiluminescent reaction can be made quite selective to $NO_2$ under suitably chosen conditions, so that other nitrogen-containing compounds such as ammonia, organic nitrite, organic nitrate, NO, and hydrocarbons do not interfere.

The disclosed method has several significant advantages over previous methods for detecting $NO_2$. In one known method, $NO_2$ is first converted to nitric oxide (NO), which is subsequently reacted with ozone ($O_3$). This reaction is also chemiluminescent, but the light emitted has a substantially different peak wavelength. Such a method requires two reaction steps and provision of a source of $O_3$, making both the method and the apparatus needed to carry it out more complicated, expensive, and difficult to implement than the present invention. Furthermore, the method is highly prone to inaccuracy, since there is no means for discriminating between (i) the relatively small amount of NO derived from the $NO_2$ from pyrolyzed explosive and (ii) ambient NO, which is a common air pollutant often present in substantially larger concentration.

The selectivity of the present system for $NO_2$ is further enhanced by providing luminol in an aqueous, alkaline solution. The luminol preferably is present at a concentration ranging from about 0.3 to 3 mM. Higher concentrations of luminol tend to absorb the emitted light, decreasing the detectable signal. Preferably, the base is provided at a concentration ranging from about $10^{-3}$ to 5 M. Use of potassium hydroxide (KOH) as the base is preferred, as it surprisingly has been found to increase the chemiluminescent light output over that resulting from solutions comprising other bases such as sodium hydroxide (NaOH). Sufficient alkalinity has been found to reduce the negative interference of ambient $CO_2$. The alkalinity is believed to counter the tendency of $CO_2$ to acidify the luminol solution. It is also preferred that the solution further comprise a sulfur compound to beneficially reduce the interference from competing reactions of luminol with $SO_2$ and $O_3$, which are also common atmospheric pollutants. Suitable sulfur compounds include $Na_2S$, $Na_2S_2O_4$, and $Na_2SO_3$. The presence of the sodium sulfite ($Na_2SO_3$) at a concentration ranging from about $10^{-3}$ to 0.1 M has been found to be particularly effective. A more preferred solution comprises $10^{-3}$ M luminol, 1.0 M KOH, and $10^{-1}$ M $Na_2SO_3$. It is also preferred that the luminol solution further comprise a chemiluminescence enhancer such as p-iodophenol to increase the intensity of the signal. The specificity of the reaction to $NO_2$ is also enhanced by the inclusion in the solution of small amounts of one or more alcohols, preferably including but not limited to, lower alcohols such as methanol, ethanol, propanol, isopropanol, and butanol.

Referring now to FIG. 1 of the drawings, there is depicted an explosive detection system 79 of the invention. A collection means comprises glass collecting tube 84, open at both ends and at least partly filled with adsorbent 96; heater 85; and the associated piping. Adsorbent 96 is preferably composed of a powder of poly(2,6-Diphenyl phenylene oxide). Such material is available commercially from the Enka Research Institute Arnhem under the tradename Tenax GC™. However, other adsorbent substrates, including non-exclusively wire mesh, glass wool, and activated carbon, may also be employed. A sample of vapor or plume in air and appointed to be tested for the presence of explosive agents is passed into tube 84 for collection on adsorbent 96. Tube 84 is subsequently placed into heater 85. One end of tube 84 is connected by air pump line 82 to mechanical air pump 81, while the opposite end of tube 84 is connected to intake port comprising inlet 97 of reaction cell 98 by transfer line 87. Heat from heater 85 is applied to glass tube 84, causing vapor to be desorbed from adsorbent 96. The vapor is swept from tube 84 by air flowing from air pump 81 and into transfer line 87, which contains a pyrolyzer 86. It will be understood that mechanical air pump 81 may be replaced by an alternate pumping source of carrier gas under pressure, such as a compressed gas cylinder. Instead of ambient air, the carrier gas may be any other oxygen-containing gas or mixture compatible with other aspects of the disclosed process. In the aspect depicted, the decomposition means comprises pyrolyzer 86, in this case a heated Pt—Rh alloy wire. Any explosive present in the vapor is catalytically pyrolyzed, producing $NO_2$ gas that enters the gas stream from air pump 81. The carrier gas, now containing any $NO_2$, resulting from pyrolysis of any explosive desorbed from adsorbent 96, is carried into reaction cell 98. Some of the $NO_2$, if present, diffuses through semi-permeable, hydrophobic membrane 90 and contacts solution 99 containing luminol. The reaction produces a molecule in an excited state that decays by chemiluminescence to produce photons having a wavelength centered at about 425 nm. A light detector, in this case comprising photomultiplier tube (PMT) 93 and an associated power supply and control and detection electronics of conventional design (not shown), detects the emitted photons and provides a digital or analog electrical signal representing the amount of light detected. Advantageously, common PMT's have substantial sensitivity in the 425 nm wavelength range. The light detector optionally incorporates an optical filter (not shown) interposed between the reaction cell 98 and PMT 93. The filter selectively transmits light having a wavelength within a preselected range encompassing the wavelengths emitted in the luminol-$NO_2$ reaction. PMT 93 is connected to a digital computer 94 for control and analysis. Computer 94 is preferably a personal computer of conventional type, but may also be a microcomputer or other similar device comprising a digitial electronic processor or general purpose computer suited for control and analysis. Preferably computer 94 also comprises a display for output and communication with an operator or system user. Computer 94 may also be networked to other computer and electronic systems in a conventional manner.

The luminol solution employed in the practice of the present invention is advantageously provided in a replaceable cartridge or scintillation vial and sealed therein by a semi-permeable, hydrophobic membrane that permits diffusion of $NO_2$ into the vial but reliably confines the luminol solution. Preferably the membrane is composed at least one of polypropylene and PTFE and has a pore size ranging from about 0.1 to 8 µm. A pore size ranging from about 4 to 6 µm is more preferred. By way of contrast, prior art luminol-based analysis systems typically employ a reservoir of luminol solution that is provided in the reaction zone either as free liquid or conveyed by a wick system. Either approach is cumbersome and entails significant drawbacks, such as those described in U.S. Pat. No. 4,765,961. The free liquid is generally pumped from a reservoir to a waste vessel by a pump such as a peristaltic pump. The pump must be maintained and the reservoir refilled, necessitating skilled expertise and the inevitable inconvenience of transferring liquid solution.

In addition, it is difficult to operate and reliably calibrate systems which provide luminol either from a wick or free liquid. In either case, the effective surface area of the liquid is subject to significant variation, leading to a proportionate change in the intensity of the chemiluminescent reaction, which occurs at liquid-gas interface or within a short diffusion distance from the surface. Free liquid may slosh for many reasons, including external vibrations and in the course of pumping of the luminol solution. The meniscus on top of the luminol source may change shape due to contaminants or irregularities of the container surface. The wicking action may likewise change as a result of particulate deposits or other interfering effects.

Supplying the luminol solution in a replaceable cartridge sealed by a semi-permeable membrane is especially advantageous for an apparatus that is intended to be portable or used in field operations such as airport baggage screening. In these applications the cartridge has a sufficient charge to allow the unit to operate for up to several weeks. The cartridge may be replaced rapidly by operators who need not be specially trained, so that far less downtime is needed for maintenance than with the previous units, for which the maintenance requires much more time and a substantially higher level of expertise. Calibration of the analysis unit is readily and accurately accomplished. The modularity of the system obviates the inconvenience and risk of spillage associated with replenishment of a liquid reservoir of the type used in previous systems. The sealed cartridge also makes the present system easier to transport or operate portably than a system having an open reservoir for the luminol solution.

In another aspect of the invention, collection of sample is accomplished by impinging infrared laser light on the surface to be scanned. Depending on the fluence of the laser light, material is removed from the surface by either desorption or ablation, or a combination thereof. The plume resulting from the incident radiation may include the contraband substance in the form of monomers, larger molecules, discrete particles of a variety of sizes, or a combination thereof. Preferably the laser illumination used in the present invention has a sufficient intensity and duration to cause either vapor or particles of contraband residue, or a combination thereof, to be thermally desorbed or ablated.

The laser light-based collection means is especially advantageous for detecting explosives and other contraband concealed within luggage, packages, cargo, and the like. A very limited number of known explosive materials, e.g. nitroglycerin, have a sufficiently high room-temperature vapor pressure to cause emission of substantial vapor even if sequestered inside a package. However, other very common explosives carry equal or greater explosive energy; yet have vapor pressures that are orders of magnitude lower. As a result, materials posing enormous potential for harm, such as SEMTEX, DM12, and C-4, emit miniscule amounts of vapor whose concentration is too low to be detected by known methods. These materials pose a grave threat in the hands of terrorists. Since the plastic explosives have little if any content of metals or other heavy elements, they exhibit little signature for x-ray detection. Moreover, they are available in a variety of physical forms, including moldable, clay-like substance and as thin sheets, making them relatively easy to disperse and hide among seemingly innocuous, ordinary objects.

Despite the importance of detecting these plastic explosives, currently practiced methods still have significant limitations and drawbacks. In one approach to facilitate tracing and to enhance the detectability of these materials, legitimate commercial and governmental manufacturers virtually always incorporate taggants having substantial vapor pressure in their products. The International Civil Aviation Organization (ICAO) has specified certain of such taggants. DMNB (2,3-dimethyl-2,3-dinitrobutane) has been identified as being especially advantageous, since it can readily be incorporated in explosives without compromising their shelf life or stability. The present system readily detects such taggants. However, illicit explosives made by terrorists or other criminal elements are highly unlikely to incorporate taggants.

Other approaches rely on the propensity of plastic explosives to transfer residues to the hands of a user and to their environs, which thereby provides avenues for detection. These explosive materials are generally composed of particles of high explosives like RDX, PETN, and HMX in a sticky, polymeric matrix. Mechanical wiping and abrasion methods can be used to collect surface samples that include these residues.

Surface residues and fingerprints contaminated by plastic explosives initially contain substantial amounts of any incorporated taggants. However, these taggants quickly evaporate, owing to their high volatility and high surface area. The amount of taggant present falls below detectable limits, often in a matter of minutes or a few hours. The reliability of a luggage screening system that relies principally or exclusively on detection of taggants is thus dubious. The present system is highly advantageous in being able to detect residues of plastic explosives, whether or not so tagged. While it is highly likely that trace residues of the high explosive constituents are present on the surface of luggage or other parcel containing high explosive, enhancement in some form is still needed to assure their detectability. Prior art detection methods have generally relied on mechanical means, such as abrasion by a wipe or brush, or a flow of gas to dislodge a sample large enough for analysis. If properly implemented, such methods can be effective. Use of the present system represents an improvement of these methods, as a result of the sensitivity, accuracy and rapidity of the luminol analysis provided therein. However, the range of applications in which any of these mechanical sample collection methods is useful is restricted by their low throughput and the difficulty of automating them. By way of contrast, the present laser-based collection system overcomes these disadvantages. It is easily automated and can operate rapidly.

The exact mechanism for the removal of material by laser is not fully understood but is believed to depend on laser fluence and pulse length or duration. A fluence ranging from about 1 to 50 $mJ/cm^2$ is presently believed suitable for the practice of the invention. At low fluences, the laser is thought to heat the material locally and raise its vapor pressure accordingly, causing thermal desorption of a plume containing principally monomers, possibly including $NO_2$ that is thermally decomposed directly. At higher fluences (e.g., fluences >3.7 $mJ/cm^2$), it is believed that the ejection mechanism changes to ablation, in which sufficient heat is released to cause ablation of discrete particles of material. In either case, a plume of vapor and/or particles is liberated that can be collected and transported to a chemical analysis detector system in accordance with the present invention. The detection system can detect $NO_2$ emanated either directly by decomposition of an explosive taggant or one or more substances in the explosive or through subsequent pyrolysis of ejected explosive particles. It is preferred that a system of the invention operating with a laser fluence that results in substantial ablation of particles further include a pyrolyzer to boost the amount of $NO_2$ evolved and available for detection. The resulting enhancement of the system's sensitivity beneficially allows explosives to be detected at a much lower level.

At much higher fluences, several problems become apparent. Accordingly, laser irradiation heretofore has generally been considered unsuitable for large-scale screening systems because of its propensity to cause perceptible damage to the substrate. Moreover, high fluence, especially in combination with long pulse duration, can produce local heating that is sufficient to cause substantial deflagration or detonation of explosive material on the surface of interest. It is preferred that the intensity and duration of the laser illumination used in the practice of the present invention not be sufficient to cause substantial deflagration or detonation of an explosive substance present on the surface being scanned. Excessive fluence may also cause decomposition of other substances of interest, such as drugs and narcotics, precluding their detection.

Careful control of fluence is also beneficial in not removing the entirety of a surface residue containing explosives during the initial mass screening of baggage items. If an item is initially identified as suspicious by the present method, the remaining residue can be further analyzed by other confirmatory forensic techniques that are more sophisticated and accurate, but entirely impractical for mass screening as too difficult, slow, and costly.

Figure 2:
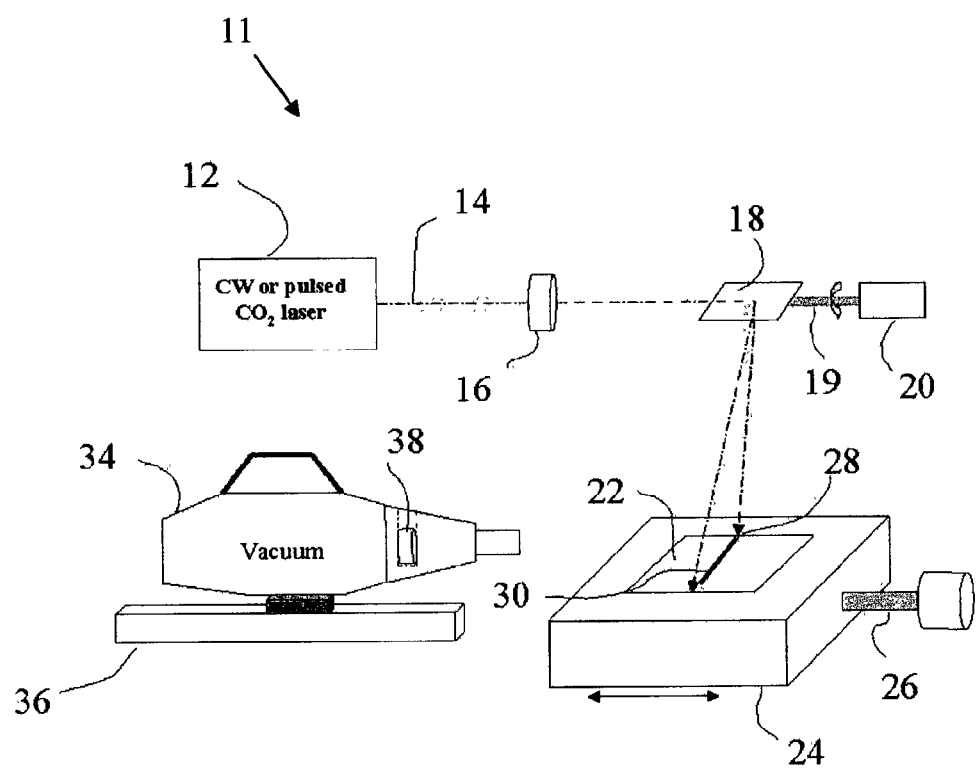
FIG. 2 is a perspective view of an explosive detection system of the invention.

One implementation of the laser light aspect can be understood by reference to FIG. 2. Therein is depicted an explosive detection system 10 of the invention. A $CO_2$ gas laser 12 emits infrared laser light along optical path 14, which passes through focusing lens 16. The light strikes mirror 18, which is mounted on rotating shaft 19 of electric motor 20. The reflected light impinges on target 22 mounted on translation stage 24, which is movable by turning drive screw 26. Rotation of mirror 18 causes the point of impingement 28 of light on target 22 to move generally along a line 30 across target 22. Vapor and particles desorbed from target 22 are collected by vacuum 34 movably mounted on rail 36.

A sample of the desorbed material is collected on a particle trap substrate 38 mounted within a collecting tube in vacuum 34 and analyzed by transferring it to an analyzer (not shown), which could be of the type depicted by FIG. 1. In other embodiments the particle trap could be directly mounted on the analyzer or be located on a rotatable carousel allowing it to be selectively positioned for different functions, such as sample collection, analysis, and cleaning.

The aspect depicted advantageously allows the light to impinge on an extended interrogation zone. However, other simpler optical systems can be employed in instances wherein only a localized interrogation zone needs to be analyzed.

It is found that infrared laser radiation is effective in causing desorption of material such as explosive residues from a surface. A number of systems capable of lasing at infrared wavelengths are known, including Nd:YAG and $CO_2$ gas, and are suitable for practice of the invention. The effectiveness of laser radiation in causing desorption is enhanced by selection of a wavelength which the suspect material is known to absorb strongly. Incident radiation having a wavelength that overlaps the absorption band is strongly absorbed, leading to strong, selective heating of the substances of interest. Laser light having a wavelength at or near a peak in a material's absorption spectrum is especially effective. Consequently, one aspect of the present invention employs a $CO_2$ gas laser, which characteristically emits radiation at several frequencies in the 9–11 μm wavelength range. The C—$NO_2$ bond, present in virtually all nitrogenous explosives, has a substantial resonant absorption in this range, making the $CO_2$ laser especially suited for use in a system for the detection of nitrogenous explosives according to the present invention.

Moreover, other materials, including the substrate, whose spectra do not exhibit strong absorption at the wavelength of the incident light, will not absorb substantially and so will not experience undue heating or other damage. Appropriate selection of wavelength thus affords selectivity, in that the material of interest is strongly and efficiently desorbed, while other materials are not markedly affected. The selectivity allows the intensity and duration of the illumination of the substrate by the laser light to be held at low levels, thereby eliminating damage to the substrate but still allowing efficient desorption of enough sample to allow reliable detection. This selectivity is highly advantageous for a screening system and overcomes the problems of surface damage heretofore presumed to be an inevitable consequence of laser illumination. The inventors have found that careful control of both laser wavelength and pulse duration and repetition rate is a highly effective means of maximizing the generation of the desired sample plume and minimizing collateral damage.

In addition, good selectivity enhances detection sensitivity by more efficiently removing desired substances, while virtually eliminating the removal of extraneous or background material, e.g., lint, dirt, or solvent, which frequently swamps detectors in prior art systems and results in the need for frequent cleaning of the collection and analysis systems. Conventional wipe-based systems are especially vulnerable to these difficulties. Laser desorption is also particularly effective in removing residue lodged in cracks and crevices of the substrate which are inaccessible by wiping.

The efficiency and selectivity of desorption may be further enhanced by altering the isotopic content of the $CO_2$ gas fill in the laser. It is known in the art that the spectral lines responsible for the laser action of a $CO_2$ gas laser entail molecular vibrations. Naturally occurring carbon is predominantly composed of atoms of a stable isotope having an atomic weight of about 12, denoted as $^{12}C$, with a slight amount of the stable isotope having atomic weight of about 13, or $^{13}C$, and lesser amounts of the unstable radioisotope $^{14}C$. Likewise, atmospheric oxygen is predominantly composed of diatomic $^{16}O_2$, with traces of $^{18}O_2$ and the mixed species $^{16}O^{18}O$. Thus, normal $CO_2$ is predominantly composed of $^{12}C$ and $^{16}O$, denoted as $^{12}C^{16}O_2$. However, techniques are known for the isotopic enrichment of both atoms, that is to say, the formation of a quantity of material in which the relative abundance of the various isotopes differs from the corresponding naturally occurring abundance. Thus, $CO_2$ gas enriched in any of the species $^{12}C^{16}O_2$, $^{13}C^{16}O_2$, $^{12}C^{18}O_2$, and $^{13}C^{18}O_2$ may be obtained. Laser action may be established in a $CO_2$ gas laser based on any of these species if present in sufficient concentration. The differences in atomic mass of the constituent atoms in each species give rise to a unique characteristic vibrational spectrum. Hence, laser operating frequencies not obtainable with normal $^{12}C^{16}O_2$ can be selected by altering the isotopic abundance in the gas charge. The efficiency and selectivity of desorption of a given contraband substance may be increased by selection of an illuminating wavelength matched as closely as possible to the particular absorption spectral lines of that substance. Thus, lasers based on $CO_2$ gas with different isotopes may be preferred for detecting particular contraband substances.

The laser radiation used in practicing this invention may be emitted continuously. Preferably, the beam of light is pulsed. Such pulsing of the light beam is preferred because higher peak power and energy density can be employed without undesirable damage to the substrate or other similar thermal side effects. The use of a short pulse duration is preferred in that heating of the residue and underlying surface is thereby localized, minimizing or eliminating unwanted surface damage.

Pulsed beams may be obtained in several ways. Light from a continuously emitting laser may be passed through an interposed mechanical chopper, which may comprise a structure such as a disk, which has transparent portions and portions which are opaque to light having the wavelength of interest. The light beam is directed through the structure, which is rotated, as by an electric motor, to periodically interrupt the optical path. The repetition rate, pulse duration, and duty cycle may be varied by changing the rotational speed of the structure and the relative amounts of the structure that are transparent and opaque. Mechanical choppers generally have about a 50% duty cycle (i.e., the fraction of time during operation in which the chopper passes light). They are especially useful for obtaining pulse repetition rates of up to about 20 kHz. This rate is generally higher than may be obtained with a pulse-mode laser. Alternatively, electro-optic cells are known which may be made transparent or opaque in response to a suitable electrical input and operate at a higher pulse rate. A pulsed beam may be obtained by interposing such a cell in the optical path of the present system and providing a suitably varying electrical input, as would be known to one skilled in the art.

More preferably, a pulsed mode laser may be employed in the practice of the invention. $CO_2$ gas lasers are known which typically give pulse duration of about 200 ns and pulse repetition rates up to about 1 kHz.

Figure 3:
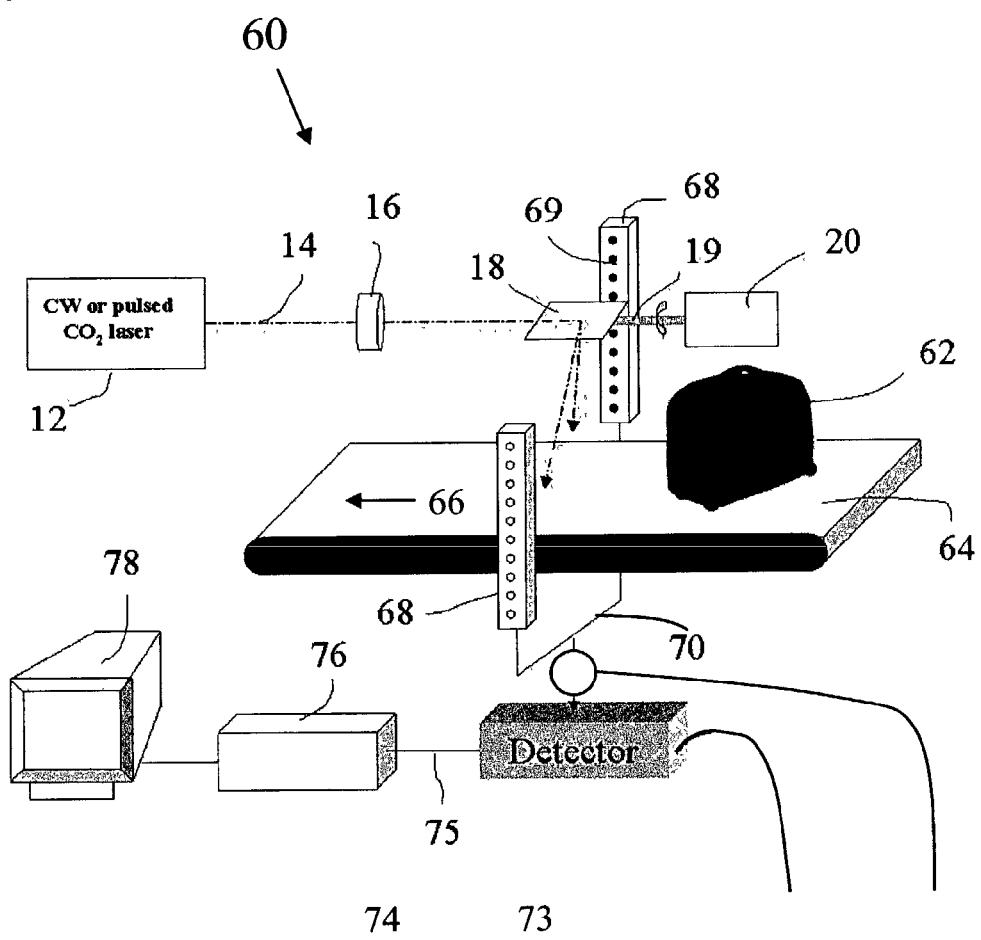
FIG. 3 is a perspective view of an automated explosive detection system for screening items of luggage.

In another aspect of the invention, depicted by FIG. 3, there is provided an automated explosive detection system 60 for screening baggage items, such as a piece of luggage 62. A $CO_2$ gas laser 12 emits infrared laser light along an optical path 14, which passes through an optical system comprising a focusing lens 16 and a mirror 18. The light strikes the mirror 18, which is mounted on a rotating shaft 19 of an electric motor 20. Items of luggage 62 are placed on a conveyor belt 64 appointed for motion along the lengthwise direction 66. Rotation of the mirror 18 causes the path of light reflected therefrom generally to traverse the width of the conveyor belt 64. In operation of the system 60, luggage 62 is conveyed to the region of traversal of light reflected from the mirror 18. Upon impingement of light onto any point of luggage 62 at which contraband residue is present, vapor and/or particles thereof are desorbed in a plume that is collected by a collection system comprising vacuum heads 68 appointed for intake of the plume through one or more inlet apertures 69. The collection system further comprises ducts 70 through which the plume is led by the action of air pump 73. The plume is urged to enter a chemical analysis system comprising detector 74 adapted to detect the presence of at least one contraband substance by use of the chemiluminescent chemical reaction between luminol and $NO_2$. Detector 74 comprises a pyrolyzer, a reaction cell containing an aqueous, alkaline luminol solution, and a PMT light detector apparatus; the detector system may be similar to the system depicted by FIG. 1. An electrical output from the PMT in detector 74 is connected by wire 75 to computer 76 associated with computer display terminal 78. Upon detection of light from the luminol reaction with $NO_2$ produced either by direct thermal decomposition of contraband at the surface of luggage 62 or by pyrolysis of particles containing a contraband substance, detector 74 outputs an electrical signal to computer 76. Computer 76 is also operably connected to motor 20 and conveyor 64. Computer 76 is appointed to activate and control each of motor 20 and conveyor 64 and receive in real time signals indicative of the position and status of each. Software present and operable in computer 76 is appointed to operate motor 20 and conveyor 64 in a coordinated manner so as to raster scan the point of impingement of light reflected from mirror 18 onto luggage 62 to define an extended, two-dimensional interrogation zone. The raster scanning is carried out by simultaneously translating the luggage 62 longitudinally on conveyor belt 64 and transversely sweeping the light beam by rotating mirror 18. Signals fed in real time indicative of the positions of the conveyor belt and mirror are used by the software to provide real-time location of the light beam impingement and correlate it with the intensity of the contraband substance signal attributable to desorption from the corresponding region of the interrogation zone. Positive indication of the detection of the contraband is given via computer display terminal 78. Preferably the information is displayed as a mapping on computer display terminal 78 indicative of the positions on the luggage at which contraband is or is not detected. More preferably the mapping is displayed superimposed on a visual representation of the luggage to provide clear indication of the location on the actual article at which contraband is being detected.

Other implementations of the optical system may also be used in the practice of the present invention. For example, the system may employ multiple lasers or beam splitters to produce one or more additional beams. Use of multiple beams impinging different regions of a sample allows a plurality of locations to be screened simultaneously. In addition, the system may comprise multiple lasers operating at different wavelengths to enhance detection of different contraband substances preferentially desorbed at different wavelengths.

The optical system may comprise known optical components including apertures, lenses, mirrors, prisms, filters, and the like, appropriate for operation at the laser's wavelength. The system may be designed using principles known to those in the art. The optical system acts to focus the light to a spot size preferably ranging from about 100 $\mu$m to 5 mm at the sample surface. The optical system may further include one or more deflecting optical components, such as a mirror, prism, diffraction grating, or other like means, at least one of which may be moved to deflect the light beam, thereby changing the location at which the beam impinges on the surface of the object being scanned and creating an extended interrogation zone. Known electrical, pneumatic, or mechanical means may be used to impart linear or rotary motion to the component and thereby extend the interrogation zone. For example, in some aspects of the invention the beam is reflected from a rotating mirror affixed to the shaft of an electric motor to extend the interrogation zone.

In addition to the aforesaid motion means comprising optical deflection of the interrogating light beam and a conveyor belt to move luggage, other motion means may also be employed, including robotic arms to hold and manipulate the luggage and gantry systems to move parts of the laser and detector systems. Additional motion means will also be apparent to one skilled in the art and fall within the scope of the present invention.

The present system comprises a collection system or collection means for collecting vapor or particles suspected to contain contraband analyte substances. In some aspects the system comprises an air delivery means such as an air pump acting either as a blower or to produce a mild or substantial vacuum, depending on its location within the collection system. The resulting air flow urges the analyte to enter the collection system through one or more inlet ports or apertures, and thence to pass through associated ducting that substantially transfer it to the reaction cell. In some implementations the collection system employs a collection substrate that may be contained in a collection tube. Furthermore, the collection tube may be removable to allow collection of the sample to be carried out at a location remote from the rest of the analytical apparatus. The tube may have only a single aperture that serves both as an entry and an exhaust point, or the tube may have separate openings to facilitate air flow through the tube. The collection substrate may be an integral part of the collection tube or a separate structure. Preferred substrates include wire meshes and glass wool. More preferred are adsorbents such as activated carbon. Most preferred is an adsorbent powder of poly(2,6-Diphenyl phenylene oxide). The use of a collection substrate advantageously allows accumulation and preconcentration of vapor or particles to enhance the system's sensitivity to weak concentrations of analyete. It is also preferred that a heater be provided to desorb sample captured on a substrate if such is used.

The collection means employed in some aspects of the present invention comprises a wipe used to collect a sample mechanically. As used herein, the term "wipe" includes disposable swabs or wipes of dry paper or cloth or similar items that are rubbed or stroked against baggage items, luggage, or shipping containers to mechanically remove or abrade surface residue. The removed residue is then tested for the presence therein of explosives or other contraband using the luminol-based system presented herein. Such wipes may also be wetted with a solvent to facilitate residue pickup. In either case, the wipe may be placed over an aperture of the collection system so that air flow or other means can transfer the analyte into the detection system.

Other mechanical means will also be apparent for collecting the analyte and transferring it for analysis, such as impingement of a high velocity flow of compressed gas to dislodge such residue from the surface of a baggage item.

Aspects of the method of the present invention using mechanical collection of sample generally comprise the steps of: (i) accumulating a sample of surface residue onto a collection substrate; (ii) heating the collection substrate to release a portion of the surface residue; (iii) pyrolyzing the released material to produce a detectable amount of $NO_2$; (iv) transferring the $NO_2$ to a reaction cell, a portion of which contains an aqueous, alkaline luminol solution separated from the rest of the reaction cell by a semi-permeable, hydrophobic membrane; (v) reacting, within the reaction cell, the $NO_2$ and the luminol in the presence of $O_2$ to produce light by chemiluminescence; and (vi) detecting the light with a light detector to indicate the detection of $NO_2$ arising from contraband within the surface residue.

In an aspect of the invention, the detector provides an electrical output signal representative of the detection of a contraband substance. Preferably the output signal has a magnitude that is proportional to the amount of a substance being detected. The detector may be adjusted and calibrated by an appropriate protocol, such as by establishing a background electrical output when it is known that no substance is actually present or by exposing the detector to a sample with a known concentration. It is then presumed that any signal above a preselected background level is indicative of the presence of a substance of interest. Alternatively, a background level may be determined dynamically during scanner operation by a known averaging protocol.

Indication of the detector signal output may be given by a wide variety of signal means known in the art. A binary "go/no go" indication may be provided using known comparator circuitry, in which the magnitude of the signal actually outputted by the detector is compared with a pre-selected detection threshold, and in response, audible or visible signals are activated, indicative of the presence or absence of a signal above the pre-selected threshold. The output of the detector may also be displayed as a quantitative reading on a digital or analog meter or bar display. The signal means may also comprise a computer display screen or terminal, which may display a reading in alphanumeric form or in an image simulating an analog mechanical meter or gage. More preferably, a quantitative output may also be given by the intensity or pattern of color displayed on a monitor such as a computer display screen or terminal. Such a visual display is preferred for embodiments of the invention in which an extended, two-dimensional interrogation area or zone is screened. In one aspect of the invention, a visual representation of the object being scanned is presented on a computer display screen and superimposed on the visual representation is a pattern or mapping, which, by variation of intensity or color, indicates the amount of contraband substance of a given type found on the corresponding area of the article surface. A mapping may use a false-color scheme to indicate different amounts detected. Alternatively, the presence of different contraband substances may be represented by different colors, intensity, or shading patterns. The signal means may also be capable of transmitting an alarm by wired or wireless transmission to alert police or other authorities to the possible detection of contraband substance The present system is also capable of detecting $NO_2$ produced by the decomposition of inorganic nitrate salts used as explosives, such as ammonium nitrate (AN) or mixtures of ammonium nitrate with fuel oil or the like (ANFO). In addition, the luminol reaction system of the present invention can be used to detect organic peroxides. Exemplary of such detection is the following reaction with a commonly used explosive material, tri-acetone tri-peroxide (TATP):

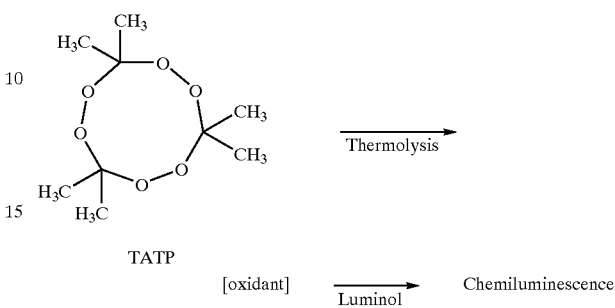

The present laser desorption and detection system may also be advantageously combined with other known scanning systems, such as magnetometric and x-ray systems, or with other systems using complementary forms of chemical analysis. A system combining the detection methods can be made more compact and efficient, thereby satisfying the detection sensitivity and throughput required for screening of passengers and hand luggage in airports, for example.

The following examples are presented to provide a more complete understanding of the invention. The specific techniques, conditions, materials, proportions and reported data set forth to illustrate the principles and practice of the invention are exemplary and should not be construed as limiting the scope of the invention.

EXAMPLE 1

Figure 4:
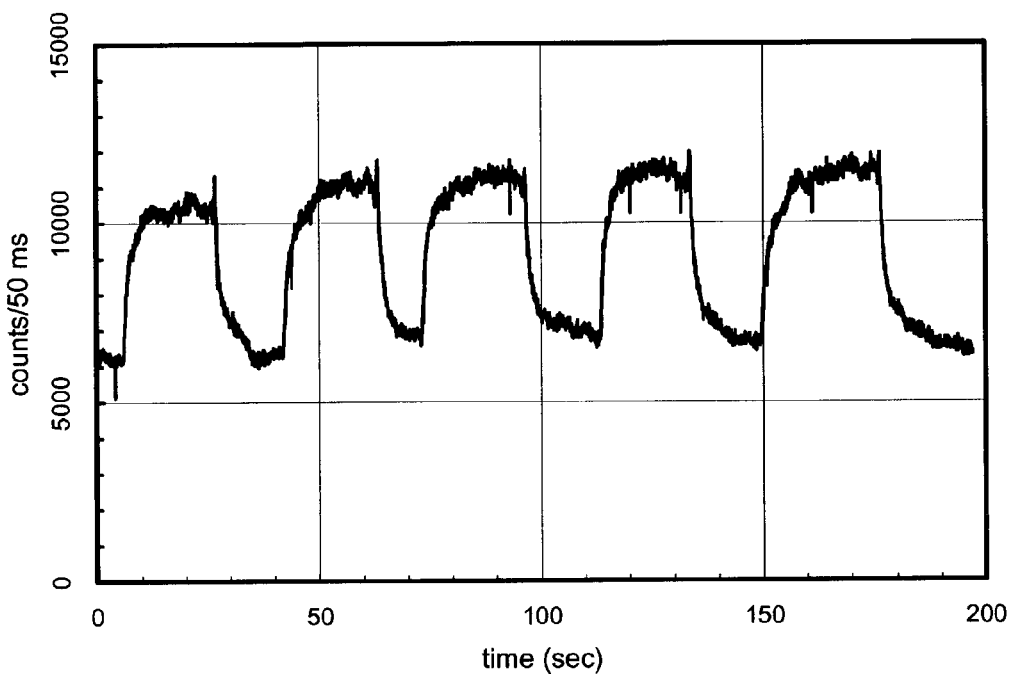
FIG. 4 is a graph depicting the observed count rate for chemiluminescent light emitted in the reaction of luminol and air alternately containing and not containing 10 ppb of $NO_2$ and detected using a detection system of the invention.

The efficacy of the luminol reaction for the detection of minute amounts of $NO_2$ was tested. Flowing, ambient laboratory air was supplied to a dilution/mixing chamber at a controlled pressure and flow rate. A small amount of $NO_2$ from a gas cylinder was alternately added or not so as to provide a test gas that alternately contained or did not contain $NO_2$ at 10 parts per billion (ppb) concentration. The test gas then passed into a reaction cell containing a piece of filter paper saturated with an alkaline, aqueous $10^{-3}$ M luminol solution that further contained 1.0 M KOH and $10^{-1}$ M $Na_2SO_3$. Light produced by the chemiluminescent reaction of the luminol and any $NO_2$ present was detected using an Electron Tubes Inc. Model P10232 commercial light detector. The unit comprised a photomultiplier tube, a high voltage power supply, a high speed amplifier-discriminator, and an embedded microcontroller. The number of counts registered by the PMT system per 50 ms increment was recorded continuously. FIG. 4 depicts the response of the detector over an extended period. A pattern approximating a square wave was seen, with the peaks coinciding with the times during which $NO_2$ was being introduced into the air carrier gas. Detection was clearly achieved at a high signal to noise ratio.

EXAMPLE 2

An experiment similar to that of Example 1 was carried out to demonstrate the detectability of the common taggant DMNB. In this case, a collection tube containing Tenax GC adsorbent was connected to a vacuum at one end to draw in a test gas which entered at the other end. The test gas, composed of laboratory air and 100 parts per trillion (ppt) of DMNB, was prepared with the same dilution system used in carrying out Example 1. The exposed collection tube, containing preconcentrated DMNB adsorbed from the above exposure was then connected at one end to a source of flowing air and at the other end to a pyrolyzer tube containing a Pt—Rh alloy wire that could be electrically heated. The collection tube was placed in a heater chamber to desorb the DMNB which was swept by the carrier gas into the pyrolyzer tube. The Pt—Rh wire was pulse heated to about 700° C. to pyrolyze the DMNB to produce $NO_2$ which was subsequently swept into a reaction cell containing a piece of filter paper saturated with an alkaline, aqueous $10^{-3}$ M luminol solution that further contained 1.0 M KOH and $10^{-1}$ M $Na_2SO_3$.

Figure 5:
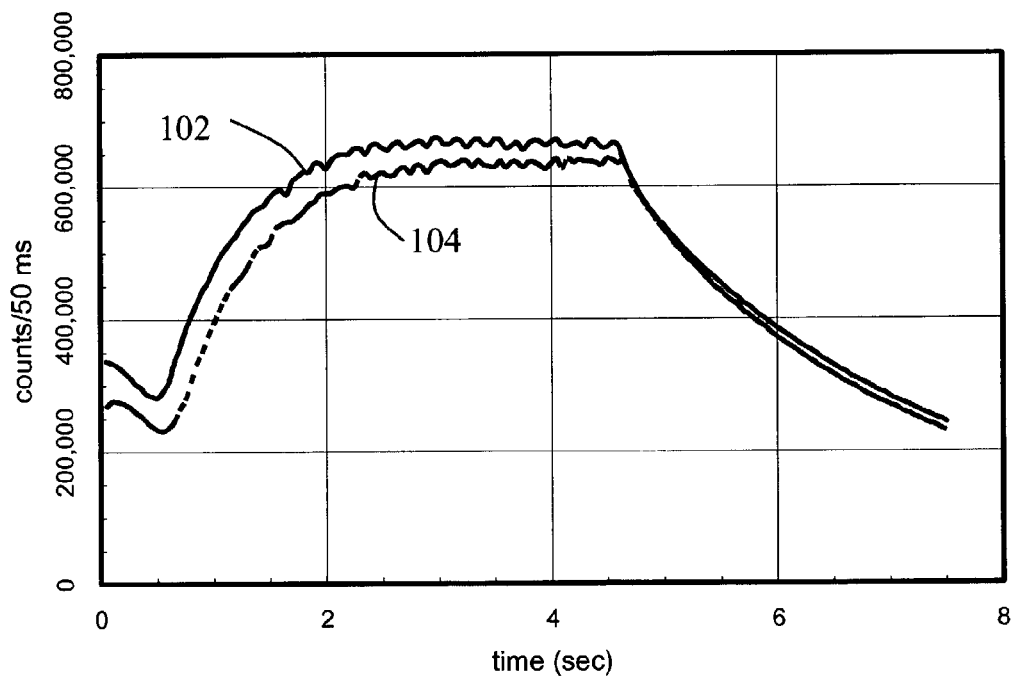
FIG. 5 is a graph depicting the observed count rate for chemiluminescent light emitted in the reaction of luminol and $NO_2$ produced by the thermal decomposition of the taggant DMNB at a concentration of 100 ppt in air, along with a blank, as determined using a detection system of the invention.

Light produced by the chemiluminescent reaction of the luminol and the $NO_2$ pyrolysis product was detected using the same light detector employed for the experiment of Example 1. The same experimental procedure was also carried out without introducing the DMNB. FIG. 5 depicts the light detected in each case, with trace 102 showing the pulse with DMNB and background trace 104 with only carrier gas. The rise in each pulse corresponds to the initiation of the pulse heating of the pyrolyzer catalyst. Without being bound by any theory, it is believed that the background trace 104 is attributable to $NO_2$ produced by direct reaction of atmospheric $N_2$ and $O_2$ in the presence of the catalytically active heated Pt—Rh wire.

As revealed by FIG. 5, DMNB is readily detected by the present system at the 100 ppt level as evidenced by a total integrated count significantly above background. The signal to noise ratio evident in FIG. 5 clearly demonstrates that DMNB would be detectable, even at levels far less than 100 ppt.

EXAMPLE 3

Figure 6:
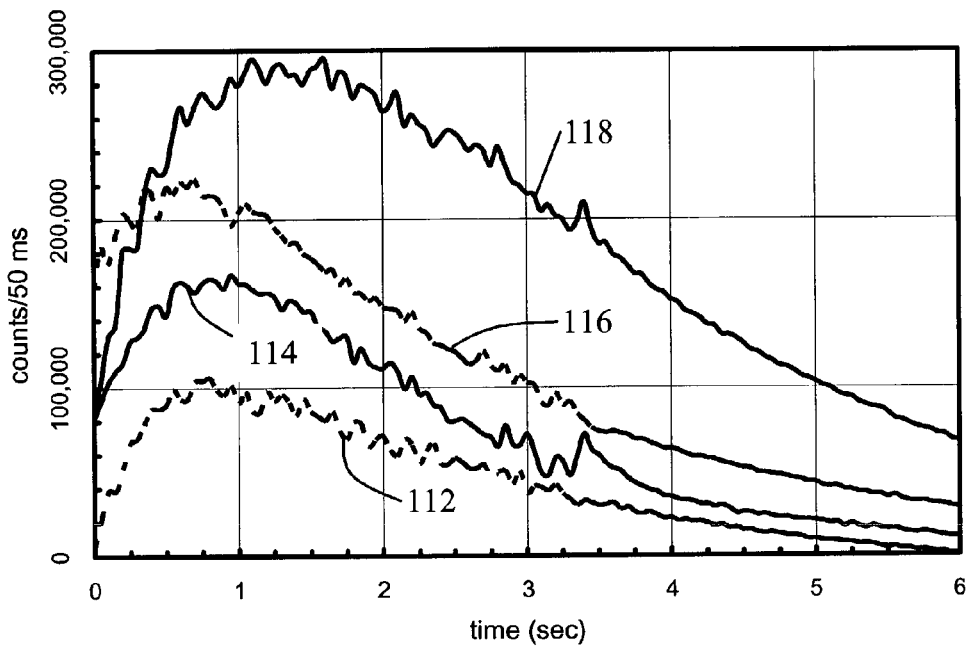
FIG. 6 is a graph depicting the observed count rate for chemiluminescent light emitted in the reaction of luminol and $NO_2$ produced by the thermal decomposition of the taggant DMNB at a series of concentrations in air, as determined using a detection system of the invention.

The experiment carried out in Example 2 was repeated using DMNB present at a series of different concentrations. FIG. 6 depicts the results of these experiments, traces 112, 114, 116, and 118 in FIG. 6 representing, respectively, concentrations of 100, 200, 500, and 1000 ppt (1 ppb), respectively. The presence of DMNB is clearly detectable at each of the concentrations, as signaled by an integrated photon count significantly over background that increased with increasing DMNB concentration.

EXAMPLE 4

A series of experiments was carried out to demonstrate the detectability of the taggant DMNB present in air at different concentrations. Samples of DMNB were collected using a protocol similar to that used in Examples 2 and 3. For each concentration, a collection tube, open at both ends and containing Tenax GC adsorbent, was exposed to a test gas, which contained DMNB at the requisite concentration prepared with the same dilution system used in carrying out Example 1. The collection tube, containing preconcentrated DMNB from the above exposure was then connected at one end to a source of flowing air and at the other end to a pyrolyzer tube containing a Pt—Rh alloy wire that could be electrically heated. The collection tube was placed in a heater chamber to desorb the DMNB which was swept by the carrier gas into the pyrolyzer tube. The Pt—Rh wire was pulse heated to about 700° C. to pyrolyze the DMNB to produce $NO_2$ which was subsequently swept into a reaction cell. A portion of the volume of reaction cell contained an alkaline, aqueous $10^{-3}$ M luminol solution that further contained 1.0 M KOH and $10^{-1}$ M $Na_2SO_3$. The luminol solution was separated from the remainder of the reaction cell volume by a semi-permeable, hydrophobic PTFE membrane. The membrane was permeable to $NO_2$, thereby allowing diffusion to bring the $NO_2$ reactably into contact with the luminol. Light emitted chemiluminescently was detected by a PMT coupled to the reaction cell.

Figure 7:
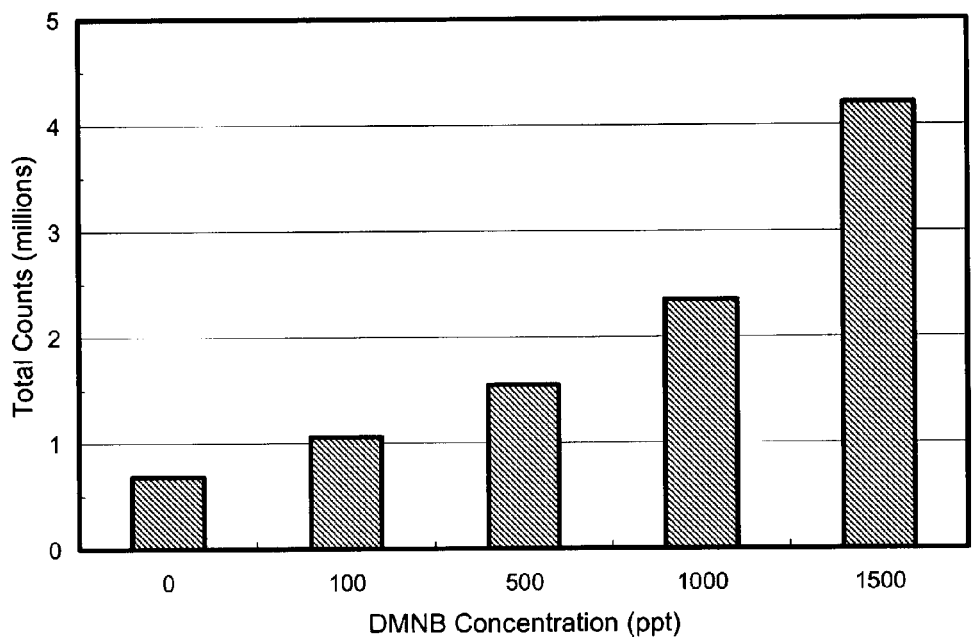
FIG. 7 is a bar graph depicting the total observed counts for chemiluminescent light emitted in the reaction of luminol and $NO_2$ produced by the thermal decomposition of the taggant DMNB at a series of compositions using a detection system of the invention employing a semi-permeable membrane.

FIG. 7 depicts the total photon count recorded by the photomultiplier tube system for the concentrations of DMNB indicated. Both the total count and the initial count rate increased with increasing DMNB. Significant increases above background were seen in the integrated photon count, even for a DMNB concentration as low as 100 ppt, confirming the efficacy of the present system in detecting DMNB taggant at minute concentration levels.

EXAMPLE 5

A series of experiments was carried out to demonstrate the detectability of the explosives EGDN and NG, as well as the taggant DMNB, each present in air at a 1 ppb concentration. Samples of each explosive and DMNB were collected and tested using techniques similar to those used in Example 4. For each material, a collection tube, open at both ends and containing a Tenax GC adsorbent, was exposed to a test gas, which contained the material at the requisite concentration and had been prepared with the same dilution system used in carrying out Example 1. The collection tube, containing the preconcentrated material from the above exposure was then connected at one end to a source of flowing air and at the other end to a pyrolyzer tube containing a Pt—Rh alloy wire that could be electrically heated. The collection tube was placed in a heater chamber to desorb each substance which was swept by the carrier gas into the pyrolyzer tube. The Pt—Rh wire was pulse heated to about 700° C. to pyrolyze the substance to produce $NO_2$ which was subsequently swept into a reaction cell. A portion of the volume of reaction cell contained an alkaline, aqueous $10^{-3}$ M luminol solution that further contained 1.0 M KOH and $10^{-1}$ M $Na_2SO_3$. The luminol solution was separated from the remainder of the reaction cell volume by a semi-permeable, hydrophobic PTFE membrane.

Figure 8:
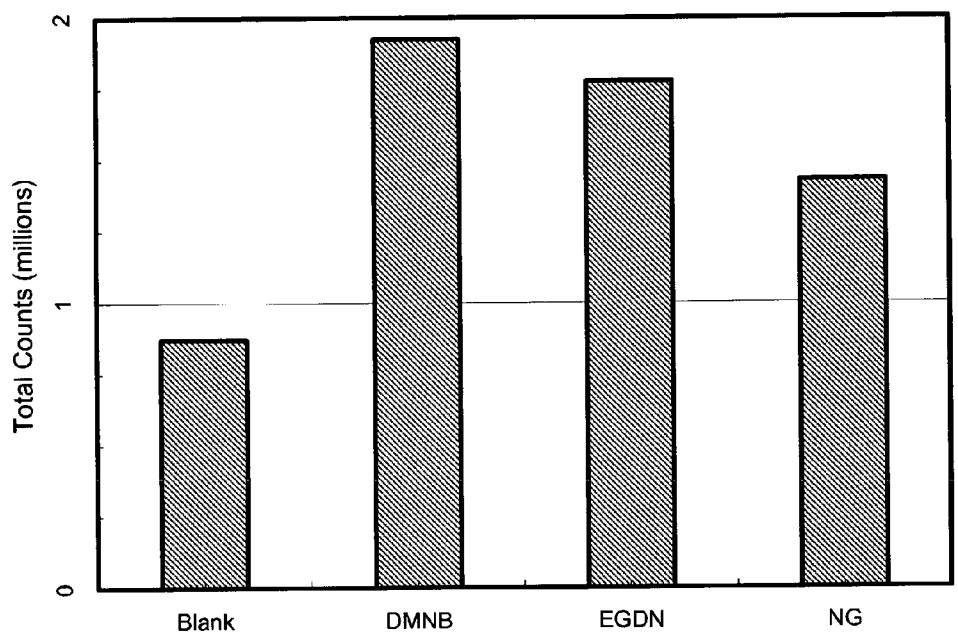
FIG. 8 is a bar graph depicting the total observed counts for chemiluminescent light emitted in the reaction of luminol and $NO_2$ produced by the thermal decomposition of the taggant DMNB and the explosives EGDN and NG in air, as determined using a detection system of the invention.

The total photon counts recorded by the PMT system are depicted in FIG. 8 for each of the substances. The corresponding values for a blank sample are also shown. It is apparent that total counts significantly above background were obtained for each substance, demonstrating the efficacy of the disclosed apparatus and method for explosive detection.

EXAMPLE 6

Figure 9:
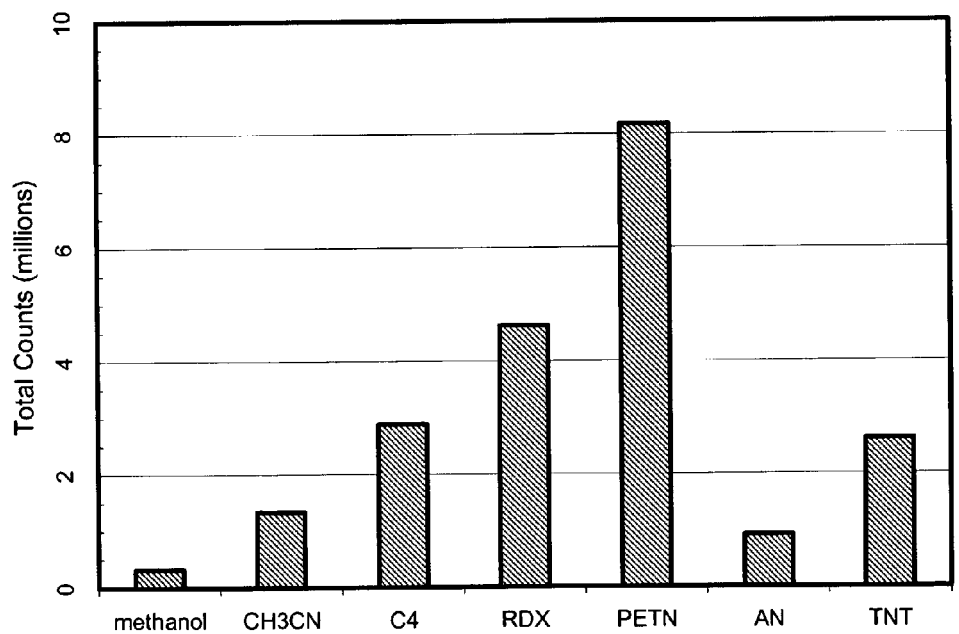
FIG. 9 is a bar graph depicting the total observed counts for chemiluminescent light emitted in the reaction of luminol and $NO_2$ produced by the thermal decomposition of a series of common explosive materials in air, as determined using a detection system of the invention.

Another series of experiments was carried out to demonstrate the detectability of various explosives collected on a collecting substrate. Samples of various explosive agents were prepared by depositing from solution 100 ng of each agent onto a stainless steel mesh disposed in a glass tube. The collected material was then heated to desorb the sample from the substrate. Each sample tube in turn was connected at one end to a source of carrier gas and at the other to the inlet of a pyrolyzer with a Pt—Rh alloy wire that would be pulse heated to a preselected temperature. The outlet of the pyrolyzer was connected to a reaction cell having a luminol solution separated from the remainder of the reaction cell by a semi-permeable, hydrophobic PTFE membrane. The solution had the same composition as that used in carrying out Example 5 above. The pyrolyzer was heated to about 700° C. for about 2 sec to produce $NO_2$ which was swept by the carrier gas into the reaction cell. The total light output from the chemiluminescent reaction of luminol and $NO_2$ was recorded for each of the agents to yield the data depicted by FIG. 9. Each of the agents gave a detectable signal substantially above background.

EXAMPLE 7

Another series of experiments was carried out to demonstrate the detectability of various explosives desorbed from a surface by laser ablation using a $CO_2$ laser.

Test targets were made by several procedures. Samples containing sticky residue from C4 and DM12 plastic explosives were made by having an operator handle the respective material for an interval and then apply a fingerprint to a glass slide to transfer residual material from his hand to the slide. A third sample was made by dissolving C4 in methanol, applying the solution to a glass slide substrate, and allowing the solution to dry. The amount of C4 explosive present on the target (about 1 $\mu$g) was inferred from the amount of solution applied and the known concentration. A fourth sample was prepared by spreading about 1 $\mu$g on a glass slide by dry transfer.

Figure 10:
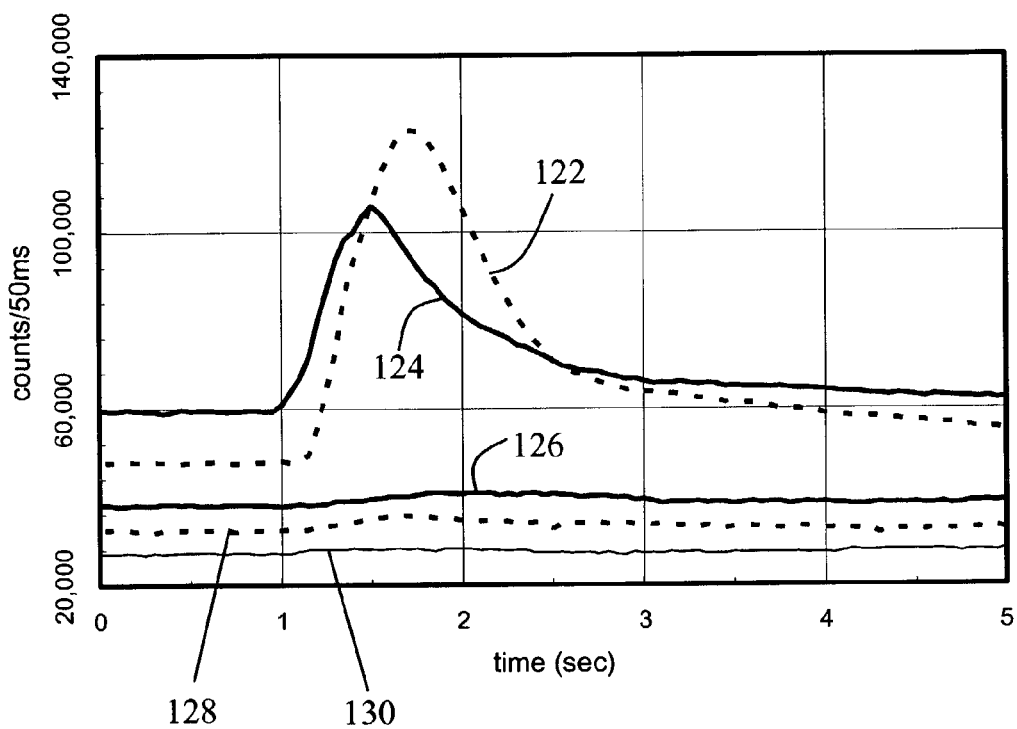
FIG. 10 is a graph depicting the observed count rate for chemiluminescent light emitted in the reaction of luminol and $NO_2$ produced by the thermal decomposition of a series of common explosives, as determined using a detection system of the invention.

Each target was tested in turn by placing it in a holder that allowed it to be illuminated by a chopped $CO_2$ gas laser and to be translated. The plume evolved was tested. The laser was a Synrad Evolution 125 unit operating in continuous mode and chopped at about 5 KHz with about a 25% duty cycle. The target was exposed to about 1000 pulses of light distributed over the surface, so that at least a portion of any nitro-explosive present on the surface would be decomposed to produce $NO_2$ without causing any appreciable damage to the substrate. The plume was drawn into a sampler situated about 10 cm from the focused spot and conveyed to a reaction cell containing an aqueous luminol solution separated from the rest of the reaction cell by a semi-permeable, hydrophobic PTFE membrane. The solution contained $10^{-3}$ M luminol, 1.0 M KOH, and $10^{-1}$ M $Na_2SO_3$. Light emitted as a result of the chemiluminescent reaction of luminol and $NO_2$ was detected by a photomultiplier tube system. FIG. 10 depicts the count rate recorded by the PMT system for substrates on which various agents had been deposited. Traces 122, 124, 126, and 128 correspond, respectively, to fingerprints of the person who had handled samples of C4 and DM12, and deposits of 1 $\mu$g of C4 from solution and 1 $\mu$g of C4 by dry transfer. Trace 130 is derived from a clean glass slide. It may clearly be seen that count rates significantly above background were seen for each of these samples containing common nitrogen-bearing plastic explosives having inherently low vapor pressures. The results demonstrate the ability of the system to detect the presence of such explosive residues on a substrate without appreciable damage thereto.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A system for screening at least a portion of the surface of a baggage item for the presence thereon of a contraband substance, the system comprising:

a. an infrared laser adapted to emit light;
  b. an optical system adapted to deliver a beam of said light emitted from said infrared laser to illuminate an interrogation area of said surface, said illumination having sufficient intensity and duration to cause selective desorption of molecules of said contraband substance present within said interrogation area without substantially damaging said surface, and at least a portion of said molecules being thermally decomposed to produce $NO_2$ molecules;
  c. a collection system having at least one aperture and being adapted to collect at least a portion of said desorbed molecules through said aperture;
  d. a reaction cell in communication with said collection system, said reaction cell having a reaction zone, an inlet for receiving in said reaction zone said molecules collected by said collection system; and an outlet for release of said air, and said reaction cell containing an alkaline, aqueous luminol-containing solution;
  e. a light detector for detecting light produced chemiluminescently by a chemical reaction between said luminol and said $NO_2$ within said reaction cell, and for outputting an electrical signal indicative of the detection of said light; and
  f. signal means for indicating the presence of said $NO_2$ produced by the decomposition of said contraband substance, said signal means being operably connected to said light detector and responsive to the receipt of said electrical signal.

2. A system as recited by claim 1, wherein said contraband substance comprises an organo-nitro explosive.

3. A system as recited by claim 1, wherein said intensity and duration of said illumination is such that at least a portion of said contraband substance is thermally decomposed to produce molecules of $NO_2$.

4. A system as recited by claim 1, wherein said intensity and duration of said illumination is such that at least a portion of said desorbed molecules is comprised in particles of said contraband substance ablated from said surface by said illumination.

5. A system as recited by claim 1, said collection system comprising an air pump for urging said desorbed molecules through said collection system and into said reaction cell.

6. A system as recited by claim 1, said collection system comprising a collection substrate on which molecules entering said collection system are accumulated and a heater to cause desorption of said accumulated molecules from said substrate.

7. A system as recited by claim 1, further comprising:

g. a pyrolyzer located between said aperture of said collection system and said inlet of said reaction cell and containing a catalyst for pyrolyzing molecules of said contraband substance to produce $NO_2$.

8. A system as recited by claim 1, wherein said catalyst is a heated wire comprising Pt.

9. A system as recited by claim 8, wherein said heated wire consists essentially of a Pt—Rh alloy.

10. A system as recited by claim 1 wherein said solution comprises luminol present at a concentration ranging from about 0.3 to 3 mM.

11. A system as recited by claim 1 wherein said solution comprises KOH present at a concentration ranging from about $10^{-3}$ to 5 M.

12. A system as recited by claim 1 wherein said solution comprises at least one sulfur compound present at a concentration ranging from about $10^{-3}$ to 0.1 M, said compound being selected from the group consisting of $Na_2S$, $Na_2S_2O_4$, and $Na_2SO_3$.

13. A system as recited by claim 1, wherein said solution comprises 1 mM luminol, 1 M KOH, and 0.1 M $Na_2SO_3$.

14. A system as recited by claim 1, wherein said solution further comprises a chemiluminescence enhancer.

15. A system as recited by claim 1, wherein said solution further comprises a lower alcohol.

16. A system as recited by claim 1, further comprising a semi-permeable, hydrophobic membrane separating said luminol-containing solution from said reaction zone.

17. A system as recited by claim 16, wherein said hydrophobic membrane consists essentially of at least one of PTFE and polypropylene.

18. A system as recited by claim 16, wherein said hydrophobic membrane has a pore size ranging from about 0.1 to 8 μm.

19. A system as recited by claim 16, wherein said solution is provided in a replaceable cartridge and sealed therein by said semi-permeable, hydrophobic membrane.

20. A system as recited by claim 1, wherein said light detector comprises a photomultiplier tube.

21. A system as recited by claim 1, further comprising:
h. a digital computer for controlling said apparatus and analyzing the output of said detector.

22. A system as recited by claim 1, further comprising:
i. motion means for relatively moving said baggage item and said beam of light to illuminate an extended interrogation zone.

23. A system as recited by claim 22, wherein said motion means comprises at least one movable optically deflecting component in said optical system which movably deflects said light to illuminate said extended interrogation zone.

24. A system as recited by claim 23, wherein said optically deflecting component is at least one rotating mirror.

25. A system as recited by claim 22, wherein said motion means comprises a conveyor belt for moving said baggage item.

26. A system as recited by claim 22, wherein said beam of light is raster scanned over said extended interrogation zone.

27. A system as recited by claim 22, wherein said signal means comprises a computer display terminal adapted to display a mapping indicative of the locations on said baggage item at which a contraband substance has been detected.

28. A system as recited by claim 27, wherein said computer display terminal is adapted to display a visual representation of said baggage item and said mapping is a false color mapping superimposed on said visual representation.

29. A system as recited by claim 1, further comprising an optical filter interposed between said reaction cell and said light detector, said filter selectively transmitting light having a wavelength within a preselected range encompassing the wavelengths emitted by said reaction between said luminol and said $NO_2$.

30. A system as recited by claim 7, wherein said pyrolyzer is pulse heated to a temperature ranging from about 300 to 800° C.

31. A system as recited by claim 30, wherein said temperature ranges from about 500 to 700° C.

32. A system as recited by claim 1, wherein said solution further comprises at least one alcohol selected from the group consisting of methanol, ethanol, propanol, isopropanol, and butanol.

33. A method of scanning at least a portion of the surface of a baggage item for the presence thereon of at least one contraband substance, the method comprising the steps of:
a. illuminating an interrogation area of said surface with infrared laser light to selectively desorb molecules of said contraband substance;
b. thermally decomposing at least a portion of said desorbed molecules to form $NO_2$;
c. passing said $NO_2$ into a reaction cell, said reaction cell having a reaction zone and comprising an aqueous, alkaline, luminol-containing solution;
d. reacting said $NO_2$ in said reaction cell with said luminol to produce light and
e. detecting said light; and
f. signaling the detection of said light to indicate the presence of said contraband substance on the surface of said baggage item.

34. A method as recited by claim 33, said reaction cell further comprising a semi-permeable, hydrophobic membrane separating said luminol solution from said reaction zone.

35. A method as recited by claim 34, wherein said luminol solution is furnished in a replaceable cartridge sealed by said semi-permeable membrane.

36. A method as recited by claim 33, wherein said illumination has an intensity and a duration such that at least a portion of said contraband substance is thermally decomposed to produce molecules of $NO_2$.

37. A method as recited by claim 33, wherein said illumination has an intensity and a duration such that a plurality of particles of said contraband substance are ablated from said surface by said illumination.

38. A method as recited by claim 33, further comprising the steps of:
g. accumulating said desorbed molecules of said contraband substance on a collection substrate; and
h. heating said collection substrate to cause desorption of said accumulated molecules from substrate.

39. A method as recited by claim 38, wherein said collection substrate comprises an adsorbent.

40. A method as recited by claim 33, further comprising the step of:
i. pyrolyzing said desorbed molecules to form $NO_2$.

* * * * *